(12) United States Patent
Migda et al.

(10) Patent No.: US 7,499,811 B2
(45) Date of Patent: Mar. 3, 2009

(54) SYSTEM AND METHOD FOR MEASURING SURFACE APPEARANCE OF A SURFACE

(75) Inventors: Francis M. Migda, Commerce Township, MI (US); Jacob Braslaw, Somerset, NJ (US); John Purcell, Livonia, MI (US)

(73) Assignee: Ford Motor Company, Dearborn, MI (US)

( * ) Notice: Subject to any disclaimer, the term of this patent is extended or adjusted under 35 U.S.C. 154(b) by 354 days.

(21) Appl. No.: 11/550,024

(22) Filed: Oct. 17, 2006

(65) Prior Publication Data

US 2008/0091360 A1   Apr. 17, 2008

(51) Int. Cl.
*G01B 3/00* (2006.01)
*G01B 5/00* (2006.01)
*G06F 19/00* (2006.01)

(52) U.S. Cl. .................................................. 702/33
(58) Field of Classification Search ................... None
See application file for complete search history.

(56) References Cited

U.S. PATENT DOCUMENTS

| | | | |
|---|---|---|---|
| 4,702,931 A | 10/1987 | Falcoff | |
| 4,715,709 A | 12/1987 | Sekine et al. | |
| 4,951,345 A * | 8/1990 | Nappi, Sr. ..................... | 15/302 |
| 4,977,853 A | 12/1990 | Falcoff et al. | |
| 4,990,261 A * | 2/1991 | Ho ............................... | 210/709 |
| 5,062,298 A | 11/1991 | Falcoff et al. | |
| 5,110,218 A * | 5/1992 | Aizawa et al. ............... | 374/153 |
| 5,240,594 A * | 8/1993 | Ho ............................... | 210/96.1 |
| 5,288,166 A * | 2/1994 | Allen et al. .................. | 404/84.1 |
| 5,328,295 A * | 7/1994 | Allen ........................... | 404/84.1 |
| 5,518,064 A * | 5/1996 | Romanowski et al. ....... | 164/453 |
| 5,584,336 A * | 12/1996 | Romanowski et al. ....... | 164/453 |
| 5,639,405 A * | 6/1997 | Erikson ........................ | 264/40.3 |
| 5,661,250 A | 8/1997 | Katahira et al. | |
| 5,707,659 A * | 1/1998 | Erikson ........................ | 425/130 |
| 5,781,008 A | 7/1998 | Muller et al. | |
| 5,959,211 A | 9/1999 | Wagner et al. | |
| 6,011,947 A * | 1/2000 | Acquaviva et al. ........... | 399/341 |
| 6,120,833 A | 9/2000 | Bonnebat et al. | |
| 6,129,079 A * | 10/2000 | French et al. ................ | 126/502 |
| 6,388,654 B1 * | 5/2002 | Platzker et al. .............. | 345/156 |
| 6,478,875 B1 | 11/2002 | Sampath et al. | |

(Continued)

OTHER PUBLICATIONS

Automatic visual inspection of the surface appearance defects of bearing roller Xian, W.; Zhang, Y.; Tu, Z.; Hall, E.L.; Robotics and Automation, 1990. Proceedings., 1990 IEEE International Conference on May 13-18, 1990 pp. 1490-1494 vol. 3 Digital Object Identifier 10.1109/ROBOT.1990.126217.*

(Continued)

*Primary Examiner*—Michael B Holmes
(74) *Attorney, Agent, or Firm*—Raymond L. Coppiellie; Brooks Kushman P.C.

(57) ABSTRACT

The embodiments described herein include a system and method for measuring a surface appearance of a surface. An appearance sensor is positionable about a surface and is configured to measure the surface appearance. A surface relationship sensor senses the distance between the appearance sensor and the surface. The appearance sensor is then positioned about the surface based on the sensed distance.

20 Claims, 3 Drawing Sheets

U.S. PATENT DOCUMENTS

| | | | |
|---|---|---|---|
| 6,484,121 | B1 | 11/2002 | Filev et al. |
| 6,502,059 | B1 | 12/2002 | Filev et al. |
| 6,528,109 | B1 | 3/2003 | Filev et al. |
| 6,532,066 | B1 | 3/2003 | Filev et al. |
| 6,543,867 | B1 * | 4/2003 | Jones .......................... 347/7 |
| 6,561,636 | B1 * | 5/2003 | Jones ......................... 347/88 |
| 6,565,200 | B1 * | 5/2003 | Jones ......................... 347/88 |
| 6,565,201 | B1 * | 5/2003 | Jones ......................... 347/88 |
| 6,572,225 | B1 * | 6/2003 | Jones ......................... 347/88 |
| 6,573,912 | B1 * | 6/2003 | Suzuki et al. ............... 715/757 |
| 6,648,435 | B1 * | 11/2003 | Jones ........................... 347/7 |
| 6,679,591 | B2 * | 1/2004 | Jones ......................... 347/84 |
| 6,687,015 | B1 | 2/2004 | Waller et al. |
| 6,701,193 | B1 | 3/2004 | Filev et al. |
| 6,705,710 | B2 * | 3/2004 | Jones et al. .................. 347/84 |
| 6,709,094 | B2 * | 3/2004 | Jones ......................... 347/88 |
| 6,719,413 | B2 * | 4/2004 | Jones ......................... 347/84 |
| 6,722,781 | B2 * | 4/2004 | Bazhenov et al. ............. 374/45 |
| 6,858,826 | B2 * | 2/2005 | Mueller et al. ........... 250/208.1 |
| 6,862,491 | B2 * | 3/2005 | Levin et al. ................. 700/121 |
| 6,864,903 | B2 * | 3/2005 | Suzuki ....................... 715/757 |
| 6,896,033 | B2 * | 5/2005 | Yamamura et al. .......... 164/428 |
| 6,936,106 | B2 | 8/2005 | Filev et al. |
| 6,961,133 | B2 | 11/2005 | Caton et al. |
| 7,054,480 | B2 * | 5/2006 | Levin et al. ................. 382/154 |
| 7,054,674 | B2 * | 5/2006 | Cane et al. .................. 600/407 |
| 7,098,435 | B2 * | 8/2006 | Mueller et al. ........... 250/208.1 |
| 7,104,635 | B2 * | 9/2006 | Jones ......................... 347/84 |
| 7,146,694 | B2 * | 12/2006 | Colson et al. ................ 29/24.5 |
| 7,159,641 | B2 * | 1/2007 | Yamamura et al. .......... 164/428 |
| 7,200,458 | B2 * | 4/2007 | Carman et al. .............. 700/117 |
| 7,359,564 | B2 * | 4/2008 | Keam et al. ................. 382/254 |
| 7,406,190 | B2 * | 7/2008 | Carman et al. .............. 382/141 |
| 7,410,737 | B2 * | 8/2008 | Levin et al. .................... 430/30 |

OTHER PUBLICATIONS

An appearance model constructed on 3-D surface for robust face recognition against pose and illumination variations R. Ishiyama; M. Hamanaka; S. Sakamoto; Systems, Man, and Cybernetics, Part C: Applications and Reviews, IEEE Transactions on vol. 35, Aug. 2005 pp. 326-334 Digital Object Identifier 10.1109/TSMCC.2005. 848193.*

Deposition of high-durability protective layers with a composite structure of DLC and GLC by facing-targets sputtering Noda, K.; Kawanabe, T.; Naoe, M.; Magnetics, IEEE Transactions on vol. 34, Issue 4, Part 1, Jul. 1998 pp. 1750-1752 Digital Object Identifier 10.1109/20.706693.*

Fractal phenomena. Dependence of hydrophobicity on surface appearance and structural features of SIR insulators Wang, X.; Yoshimura, N.; Dielectrics and Electrical Insulation, IEEE Transactions on [see also Electrical, IEEE Transactions on] vol. 6, Issue 6, Dec. 1999 pp. 781-791 Digital Object Identifier 10.1109/94. 822015.*

In Vivo Quantitative Evaluation of Skin Ageing by Capacitance Image Analysis Bevilacqua, A.; Gherardi, A.; Guerrieri, R.; Application of Computer Vision, 2005. WACV/MOTIONS '05 vol. 1. Seventh IEEE Workshops on vol. 1, Jan. 5-7, 2005 pp. 342-347 Digital Object Identifier 10.1109/ACVMOT.2005.61.*

Welding characteristics of Ag-based contact material under automobile lamp load Xiangjun, L.; Feng Xiao; Fei Hongjun; Electrical Contacts, 2003. Proceedings of the Forty-Ninth IEEE Holm Conference on Sep. 8-10, 2003 pp. 145-149.*

Study on hydrophobicity recovery characteristics and mechanism of HTV silicone rubber after corona deterioration Ying Liang; Lijian Ding; Kun Yang; Li, C.R.; Youping Tu; Electrical Insulation and Dielectric Phenomena, 2007. CEIDP 2007. Annual Report—Confernece on Oct. 14-17, 2007 pp. 308-311 Digital Object Identifier 10.1109/CEIDP.2007.4451.*

Automatic visual inspection of the surface appearance defects of bearing roller Xian, W.; Zhang, Y.; Tu, Z.; Hall, E.L., Robotics and Automation, 1990. Proceedings., 1990 IEEE International Conference on May 13-18, 1990 pp. 1490-1494 vol. 3 Digital Object Identifier 10.1109/ROBOT.1990.126217.*

Testing the failure parameters on contact surfaces of electrical equipment with binocular 3D vision technology Liu Jiaomin; Lu Jianguo; Wei Shize; Zhou Yusheng; Intelligent Processing Systems, ICIPS '97. IEEE International Conference on vol. 2, Oct. 28-31, 1997 pp. 1423-1426 vol. 2 Digital Object Identifier 10.1109/ICIPS.1997. 669252.*

On-line texture analysis for flat products inspection. Neural nets implementation Fernandez, C.; Fernandez, S.; Campoy, P.; Aracil, R.; Industrial Electronics, Control and Instrumentation, 1994. IECON '94., 20th International Conference on vol. 2, Sep. 5-9, 1994 pp. 867-872 vol. 2 Digital Object Identifier 10.1109/IECON.1994. 397901.*

Vision system for on-line surface inspection in aluminum casting process Fernandez, C.; Platero, C.; Campoy, P.; Aracil, R.; Industrial Electronics, Control, and Instrumentation, 1993. Proceedings of the IECON '93., International Conference on Nov. 15-19, 1993 pp. 1854-1859 vol. 3 Digital Object Identifier 10.1109/IECON.1993. 339356.*

A robust machine vision system design to facilitate the automation of surface appearance inspections Parker, J.M.; Advanced Intelligent Mechatronics, 2001. Proceedings. 2001 IEEE/ASME International Conference on vol. 1, Jul. 8-12, 2001 pp. 87-92 vol. 1 Digital Object Identifier 10.1109/AIM.2001.936435.*

Lightweight Structures B.V., lightweight engineering, vacuum infusion, etc., http://www.lightweight-structures.com/index. php?option=com_content&task=view&id=73&Itemid=70, Sep. 15, 2006, 14 pages.

BYK-Gardner, micro-gloss, http://products.margreff.de/?pgroup=1 &pg, Sep. 8, 2006, 5 pages.

* cited by examiner

SYSTEM AND METHOD FOR MEASURING SURFACE APPEARANCE OF A SURFACE

TECHNICAL FIELD

The present invention relates to a system and method for measuring the surface appearance of a surface.

BACKGROUND

The application of paint to objects such as vehicle bodies is a sensitive process. The quality, durability, and color matching of the paint are important in producing a high quality product. In order to maintain quality, the surface appearance of the vehicle body is measured. Conventionally, the surface appearance is measured using a hand held imaging system that qualitatively measures surface appearance. These sensors are handled by an operator who must manually apply the sensor against the surface of the body of the vehicle in the position normal to the surface. Although these sensors are useful, there exists a wide horizon for improvement. Particularly, the use of these sensors are limited by an operator's inconsistencies in not accurately placing or aiming the sensor toward the vehicle body, which produces unreliable quantitative measurements for paint process control. Accordingly, the surface appearance measurements are typically inaccurate. Because a significant reliance is placed upon the operator, a significant amount of error is introduced in the quality control of the paint process.

The embodiments described herein were conceived in view of these and other disadvantages of conventional systems.

SUMMARY

The embodiments described herein provide a system and method for measuring a surface appearance of a surface. The system includes an appearance sensor being positionable about a surface and being configured to measure the surface appearance. A surface relationship sensor is included that senses the distance between the appearance sensor and the surface. Accordingly, the surface relationship sensor provides a signal to the appearance sensor that corresponds to the distance. The appearance sensor is then positioned about the surface in response to the signal.

The method for measuring the surface appearance of a surface includes sensing a distance between an appearance sensor and the surface through the use of a surface relationship sensor. The method also includes generating a signal for the surface relationship sensor that corresponds to the distance. Additionally, the method includes positioning the appearance sensor about the surface in response to the signal. The method further includes measuring the surface appearance through the use of the appearance sensor.

BRIEF DESCRIPTION OF THE DRAWINGS

The features of the present invention which are believed to be novel are set forth with particularity in the appended claims. The present invention, both as to its organization and manner of operation, together with further advantages thereof, may be best understood with reference to the following description, taken in connection with the accompanying drawings in which:

DETAILED DESCRIPTION OF THE PREFERRED EMBODIMENT(S)

As required, detailed embodiments of the present invention are disclosed herein. However, it is to be understood that the disclosed embodiments are merely exemplary of the invention that may be embodied in various and alternative forms. The figures are not necessarily to scale, and some features may be exaggerated or minimized to show details of particular components. Therefore, specific functional details disclosed herein are not to be interpreted as limiting, but merely as a representative basis for the claims and/or as a representative basis for teaching one skilled in the art to variously employ in the present invention.

Figure 1:
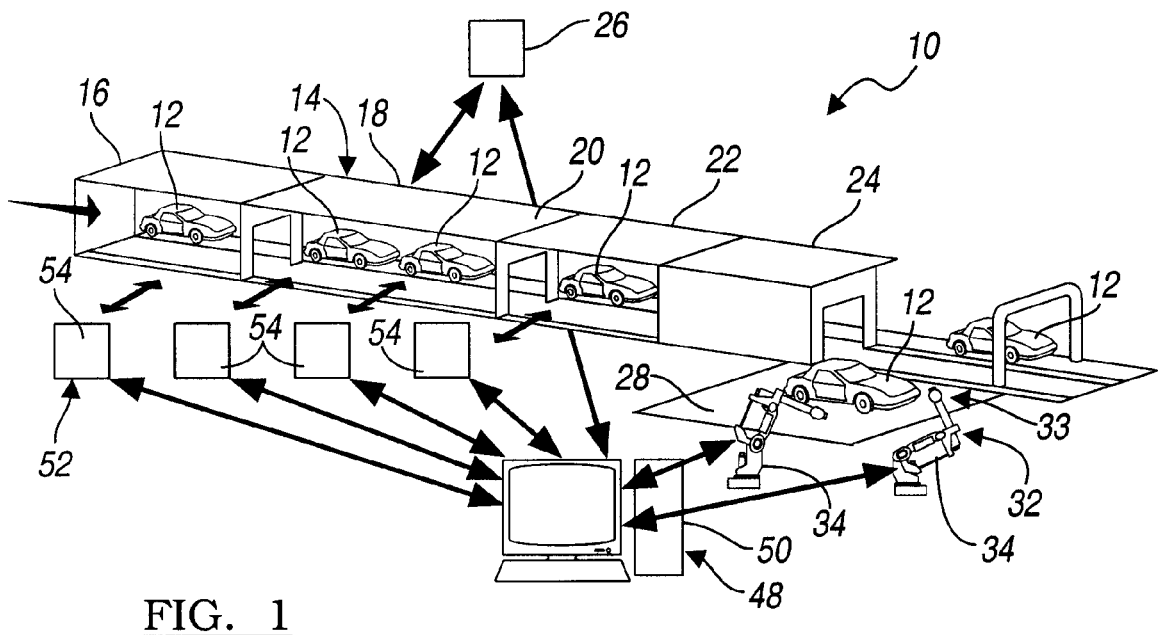
FIG. 1 is a diagrammatic view of a system for automatically measuring paint film thickness and surface appearance of painted bodies, according to an embodiment of the present invention.
Figure 2:
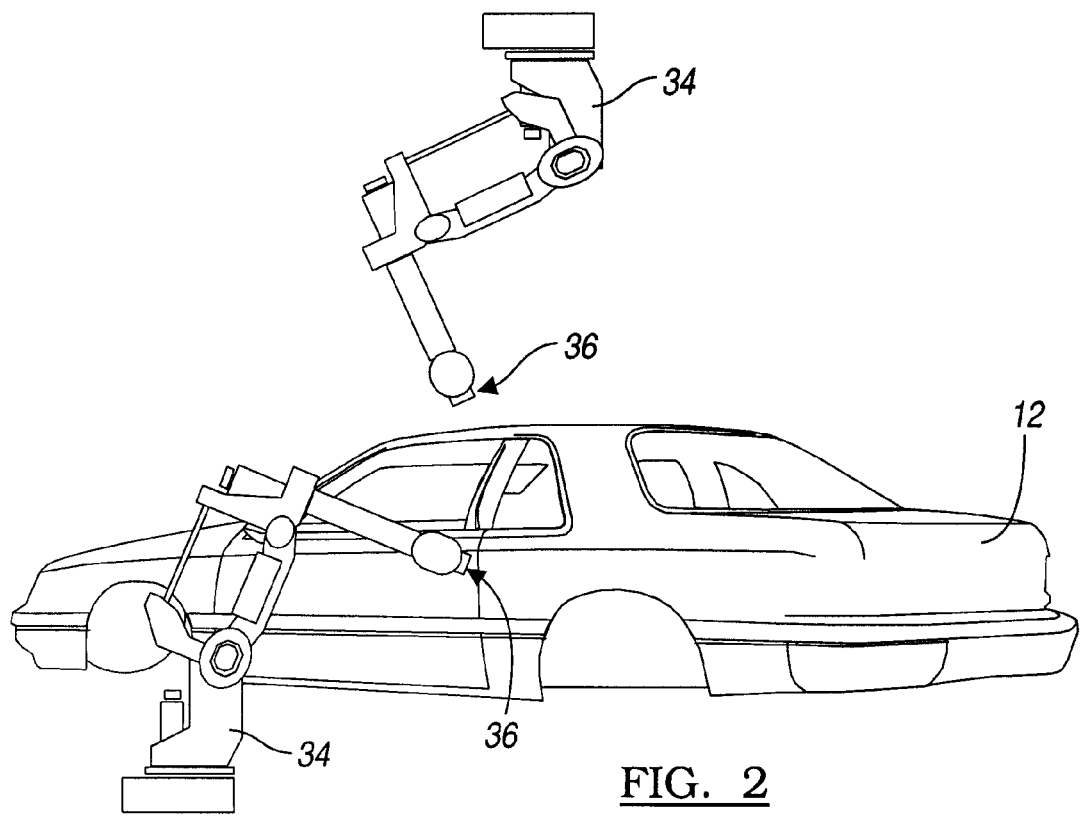
FIG. 2 is a diagrammatic view of a portion of the system of FIG. 1.

Referring to the drawings and in particular FIG. 1, one embodiment of a system 10 for automatically measuring paint film thickness and surface appearance of painted bodies 12 is shown. The painted bodies 12 are vehicle bodies for motor vehicles (not shown). The system 10 automatically measures film thickness and surface appearance on a surface of the painted bodies 12 and feedbacks information for controlling the paint process for the vehicle bodies. The system 10 is configured to measure the surface appearance of a body having multiple layers of paint film to control the paint process for each layer of the painted bodies 12.

As recognized by one of ordinary skill in the art, a surface appearance of a surface refers to the look of the surface. For example, the surface appearance may be described by terms such as glossy, dull, smooth, and the like. The embodiments described herein utilize an appearance sensor that is configured to generate signals, which are reflected by a surface and measured to quantify the surface appearance of that surface. The appearance sensor of the present invention is mounted on an operating end of a robotic arm. A hand-held embodiment of a surface appearance device is a wave-scan distinction of image (DOI) device available from BYK-Gardner, 9104 Guilford Road, Columbia, Md., 21046. Unlike the hand-held embodiment described above, FIG. 3B illustrates an embodiment of the present invention that includes a robot 50 having an operating end 50a with a sensor tool 36 for measuring surface appearance.

As will be described hereinafter, the sensor tool 36 also includes a surface relationship sensor for positioning the sensor tool 36 about a surface. The surface relationship sensor senses the relationship (i.e., distance) between the surface appearance sensor and the surface of a body. The surface relationship sensor may be a proximity sensor, an ultrasonic sensor, a camera and the like.

Figure 5:
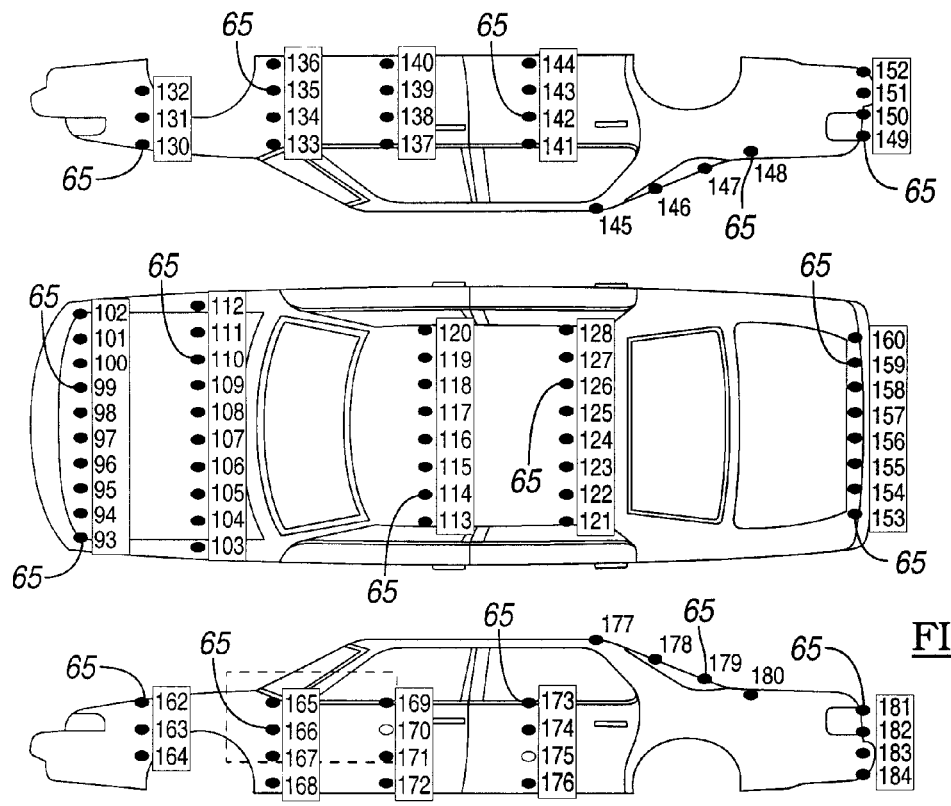
FIG. 5 is an illustration of exemplary surface locations at which the surface appearance of a surface may be measured.

Now, referring to FIGS. 1 and 5, the system 10 includes a paint booth, generally indicated at 14. The paint booth 14 includes a plurality of zones 16,18,20,22,24. The paint booth 14 includes a base coat (B/C) bells zone 16 and a base coat reciprocation (B/C Recips) zone 18 adjacent the B/C bells zone 16. The paint booth 14 also includes a first clear coat (C/C) bells zone 20 adjacent the B/C Recips zone 18 and a second C/C bells zone 22 adjacent the first C/C bells zone 20. The paint booth 14 includes an oven zone 24 adjacent the second C/C bells zone 22. The paint booth 14 includes an airflow control 26 such as fans and dampers to control the airflow in the zones 16,18,20,22,24. It should be appreciated that the paint booth 14 is conventional and known in the art.

The system 10 includes a conveyor station or measurement cell 28 located adjacent to the end of the oven zone 24 of the paint booth 14 for automatically measuring paint film thickness on the painted vehicle bodies 12. The system 10 includes a conveyor control system 30 (FIG. 4) having a conveyor (not shown) for moving the painted bodies 12 off-line to and from the cell 28 and a conveyor (not shown) of the paint booth 14.

As shown in FIGS. 1 through 4, the system 10 also includes an AutoPelt system 32 for measuring paint film thickness on the vehicle bodies 12 off-line in the cell 28. An appearance measurement system 33 is also included for measuring the surface appearance of the vehicle bodies 12. The AutoPelt system 32 and appearance measurement system 33 include at least one, preferably a plurality of robots 34 and a sensor tool 36 attached to an operating end of the robots 34.

The sensor tool 36 includes at least one, preferably a plurality of ultrasonic pulse echo layer thickness (PELT) sensors (not shown), an appearance sensor 38, and a surface relationship sensor 40. It is recognized however, that in alternative embodiments, the PELT sensors, the appearance sensor 38, and the surface relationship sensor 40 or any combination thereof, may be installed on separate robots without departing from the scope of the present invention.

The sensor tool 36 on the robots 34 aligns the PELT sensors, the appearance sensor 38, and the surface relationship sensor 40 to specific locations on surfaces of the painted bodies 12. FIG. 5 illustrates various locations at which the appearance measurement (and film thickness measurement) may take place. A plurality of locations 65 indicate positions on the surface of a vehicle in which the robots 34 align the PELT sensors, the appearance sensor 38, and the surface relationship sensor 40. In one embodiment, the film thickness is initially measured, via the PELT sensors, at the numbered locations 65, which are labeled 93-184. Once the film thickness is measured, the sensor tool 36, having the surface relationship sensor 40, is precisely re-positioned about the surface of the body at the same locations (e.g., locations 65) at which the film thickness was measured. Once re-positioned, the sensor tool 36, having the appearance sensor 38, measures the surface appearance of the surface. It should be appreciated that the number and location of the measurements will depend on the size of the painted body 12 and the paint application process. Accordingly, a contact-less surface appearance measurement is conducted through the use of the described embodiments.

Figure 3A:
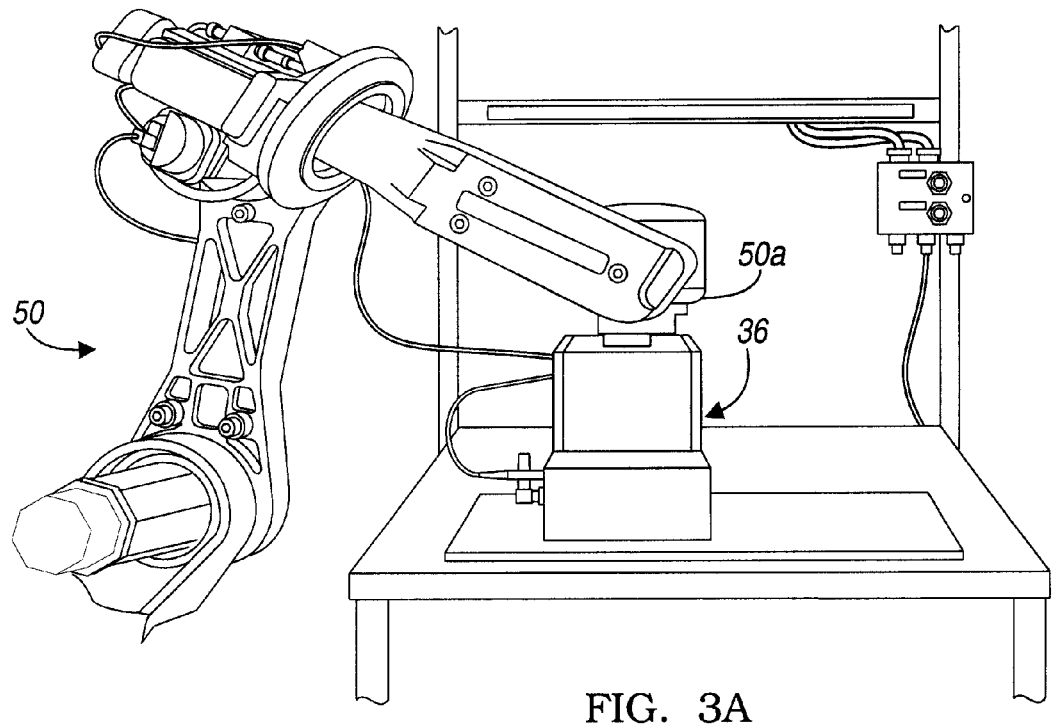
FIG. 3A is a diagrammatic view of another portion of the system of FIG. 1.
Figure 3B:
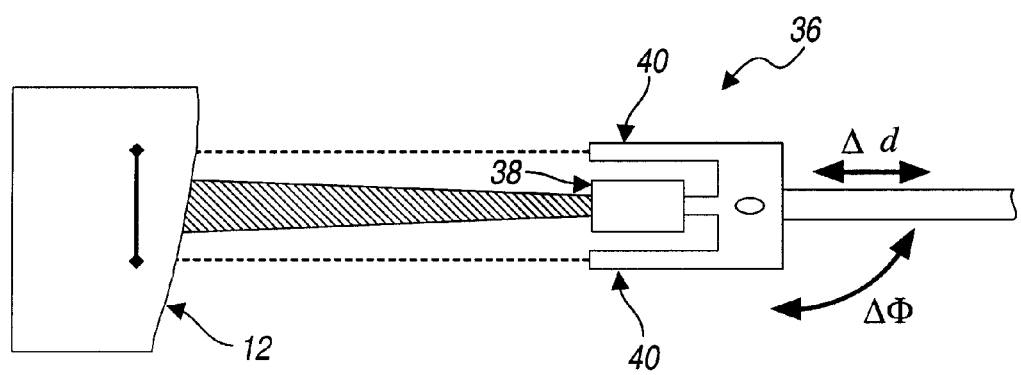
FIG. 3B is a illustration o yet another portion of the system of FIG. 1.

FIG. 3B illustrates a detailed embodiment of the operating end of the sensor tool 36 having the appearance sensor 38 and the surface relationship sensor 40. As described above, the surface relationship sensor 40 is configured to sense the distance between the sensor tool 36 (i.e., the appearance sensor 38) and the surface of the body 12. Upon sensing the distance, the appearance sensor 38 sends a signal indicative of the distance to the appearance sensor 38 and the robot arm. In response, the robot arm positions the appearance sensor 38 about the surface of the body 12 at the desired location having an optimal distance and angle with respect to the surface. In some embodiments, the appearance sensor is positioned about the surface at an angle in a range of 85° to 95° with respect to the surface of the body. Preferably, the appearance sensor is positioned about the surface at an angle of 90°. The appearance measurement system described herein is calibrated to automatically adjust the reflected signal for varying the distance between the sensor tool 36 and the surface of the body 12. As such, surface measurements are expedited because accurate positioning of the sensor tool 36 is automated. Accordingly, the appearance sensor may be automatically positioned within 10 centimeters (cm) of the surface of the body.

The surface appearance is then measured without contacting the surface of the body 12. Additionally, unlike conventional systems, the present embodiments are not subject to errors associated with manual placement of appearance measurement devices. It is also recognized that in alternative embodiments, the appearance measurement may be taken first followed by the measuring of film thickness. In such a case, the film thickness will be measured at the same locations as the appearance measurements.

Figure 4:
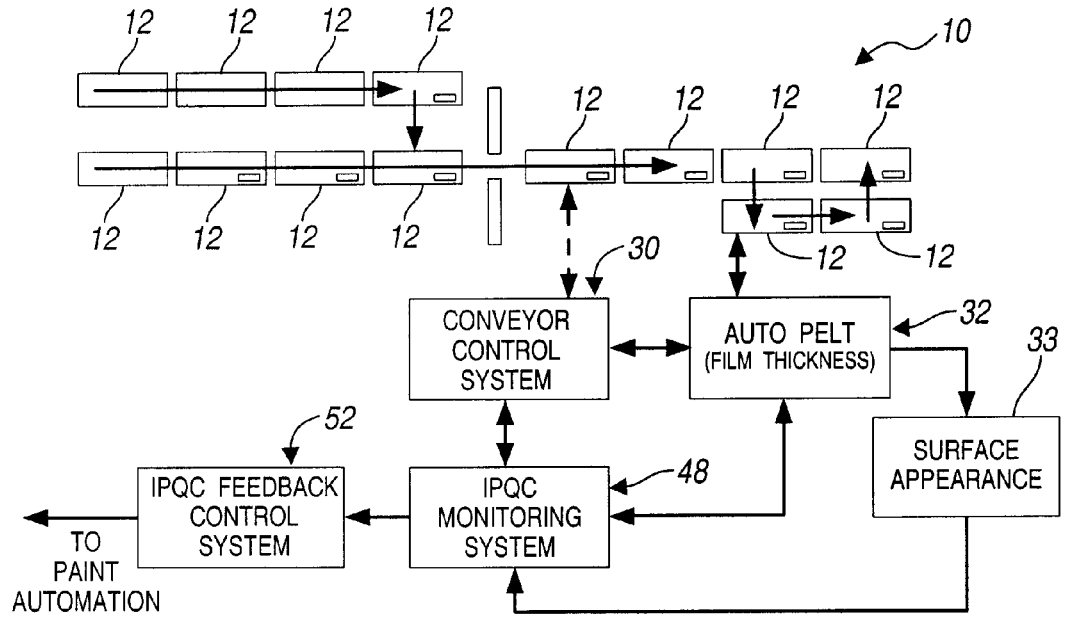
FIG. 4 is a block diagram of the system of FIG. 1.

As shown in FIGS. 1 and 4, the system 10 includes an integrated paint quality control (IPQC) monitoring system 48 connected to the AutoPelt system 32 and the surface appearance system 33. The AutoPelt system 32 and surface appearance system 33 provide the IPQC monitoring system 48 paint film thickness information and surface appearance information. The IPQC monitoring system 48 includes a computer system 50, which includes a computer having a memory, a processor, a display, and user input mechanism, such as a mouse or keyboard. The IPQC monitoring system 48 collects all inputs such as applicator flow rates, shaping air, high voltage, bell speed, and outputs information such as film thickness distribution and surface appearance across the vehicle body, for each painted body 12 that is measured.

The system 10 further includes an integrated paint quality control (IPQC) feedback control system 52 such as a programmable logic controller (PLC) 54, connected to the IPQC monitoring system 48, which receives the output information from the IPQC monitoring system 48. The IPQC feedback control system 44 outputs to and controls paint automation equipment such as the paint applicators, airflow control, etc. of the paint booth 14 based on the output from the IPQC monitoring system 48.

In general, a painted body 12 enters the cell 28 and the fixture 40 is placed on desired coordinates of the painted body 12. The computer system 42 of the AutoPelt system 32 communicates with the software of the sensor controls 44 until all designated areas are measured. The film thickness and surface appearance measurement information is then fed back to the computer system 50 of the IPQC monitoring system 48 to adjust the paint application parameters. The painted body 12 is then released back onto the moving conveyor of the paint booth 14. It should be appreciated that the number and location of the measurements will depend on the size of the painted body 12 and the paint application process.

While the best mode for carrying out the invention has been described in detail, those familiar with the art to which this invention relates will recognize various alternative designs and embodiments for practicing the invention as defined by the following claims.

What is claimed:

1. A system for measuring a surface appearance of a surface, the system comprising:
    an appearance sensor being positionable about the surface and being configured to measure the surface appearance;
    a surface relationship sensor for sensing the distance between the appearance sensor and the surface, the surface relationship sensor providing a signal to the appearance sensor that corresponds to the distance; and
    wherein the appearance sensor is positioned about the surface in response to the signal.

2. The system of claim 1, wherein the surface relationship sensor is a proximity sensor.

3. The system of claim 1, wherein the surface relationship sensor is an ultrasonic sensor.

4. The system of claim 1, further comprising an integrated paint quality control system (IPQCS), wherein the IPQCS receives signals from the appearance sensor and the surface relationship sensor, the IPQCS controlling paint quality of the surface in response to the received signals.

5. The system of claim 1, wherein the appearance sensor being positionable about the surface includes the appearance sensor being positioned at an angle in a range of 85° to 95° with respect to the surface.

6. The system of claim 5, wherein the appearance sensor being positionable about the surface includes the appearance sensor being positioned within 10 centimeters (cm) of the surface.

7. The system of claim 1, further comprising a robotic arm having an operating end, wherein the appearance sensor and the surface relationship sensor are attached to the operating end of the robotic arm.

8. The system of claim 1, wherein the appearance sensor being configured to measure the surface appearance includes the appearance sensor being configured to transmit a plurality of signals that are reflected by the surface and the appearance sensor measuring the reflected signals.

9. A method for measuring the surface appearance of a surface, the method comprising:
sensing a distance between an appearance sensor and the surface through the use of a surface relationship sensor;
generating a signal that corresponds to the distance;
positioning the appearance sensor about the surface in response to the signal; and
measuring the surface appearance through the use of the appearance sensor.

10. The method of claim 9, wherein the surface relationship sensor is a proximity sensor.

11. The method of claim 9, wherein the surface relationship sensor is an ultrasonic sensor.

12. The method of claim 9, further comprising:
receiving feedback signals from the appearance sensor and the surface relationship sensor at an integrated paint quality control system (IPQCS); and
controlling paint quality of the surface in response to the feedback signals through the use of the IPQCS.

13. The method of claim 9, wherein positioning the appearance sensor about the surface includes positioning the appearance sensor at an angle in a range of 85° to 95° with respect to the surface.

14. The method of claim 13, wherein positioning the appearance sensor about the surface includes positioning the appearance sensor within 10 centimeters (cm) of the surface.

15. The method of claim 9, further comprising attaching the appearance sensor and the surface relationship sensor to an operating end of a robotic arm.

16. The method of claim 9, wherein measuring the surface appearance through the use of the appearance sensor includes transmitting a plurality of signals that are reflected by the surface and the appearance sensor measuring the reflected signals.

17. A system for measuring a surface appearance of a vehicle body surface, wherein the system includes a robotic arm having an operating end, the system comprising:
an appearance sensor attached to the operating end, the appearance sensor being positionable about the vehicle body surface and being configured to measure the surface appearance, wherein the surface appearance is measured by transmitting a plurality of signals that are reflected by the surface, wherein the appearance sensor measures the reflected signals;
a proximity sensor attached to the operating end, the proximity sensor sensing the distance between the appearance sensor and the vehicle body surface, the proximity sensor providing a signal to the appearance sensor that corresponds to the distance; and
wherein the appearance sensor is positioned about the vehicle body surface in response to the signal.

18. The system of claim 17, further comprising an integrated paint quality control system (IPQCS), wherein the IPQCS receives signals from the appearance sensor and the proximity sensor, the IPQCS controlling paint quality of the vehicle body surface in response to the received signals.

19. The system of claim 17, wherein the appearance sensor being positionable about the vehicle body surface includes the appearance sensor being positioned at an angle in a range of 85° to 95° with respect to the vehicle body surface.

20. The system of claim 17, wherein the appearance sensor being positionable about the vehicle body surface includes the appearance sensor being positioned within 10 centimeters (cm) of the vehicle body surface.

* * * * *